US012568565B2

(12) United States Patent
Li

(10) Patent No.: US 12,568,565 B2
(45) Date of Patent: Mar. 3, 2026

(54) LAMP CONTROL METHOD, SLEEP MONITORING METHOD AND DEVICE BASED ON BIOMETRIC DATA

(71) Applicant: Homeradar ShenZhen Technology Co., Ltd, Shenzhen (CN)

(72) Inventor: Yixuan Li, Shenzhen (CN)

(73) Assignee: Homeradar ShenZhen Technology Co., Ltd, Shenzhen (CN)

( * ) Notice: Subject to any disclaimer, the term of this patent is extended or adjusted under 35 U.S.C. 154(b) by 189 days.

(21) Appl. No.: 18/661,617

(22) Filed: May 11, 2024

(65) Prior Publication Data

US 2026/0025893 A1     Jan. 22, 2026

(51) Int. Cl.
| | |
|---|---|
| *H05B 47/115* | (2020.01) |
| *A61B 5/00* | (2006.01) |
| *A61B 5/0507* | (2021.01) |
| *A61B 5/08* | (2006.01) |
| *A61B 5/11* | (2006.01) |
| *G01S 13/58* | (2006.01) |
| *G01S 13/88* | (2006.01) |
| *H05B 47/17* | (2020.01) |

(52) U.S. Cl.
CPC .......... *H05B 47/115* (2020.01); *A61B 5/0507* (2013.01); *A61B 5/0816* (2013.01); *A61B 5/1123* (2013.01); *A61B 5/1126* (2013.01); *A61B 5/4809* (2013.01); *A61B 5/4812* (2013.01); *A61B 5/7271* (2013.01); *G01S 13/589* (2013.01); *G01S 13/88* (2013.01); *H05B 47/17* (2020.01)

(58) Field of Classification Search
CPC ..... H05B 47/115; H05B 47/17; A61B 5/0507; A61B 5/0816; A61B 5/1123; A61B 5/1126; A61B 5/4809; A61B 5/4812; A61B 5/7271; G01S 13/589; G01S 13/88
See application file for complete search history.

(56) References Cited

U.S. PATENT DOCUMENTS

2021/0298643 A1* 9/2021 Baker ................... A61B 5/1113
2023/0013814 A1* 1/2023 Siva ...................... A61B 5/1116

FOREIGN PATENT DOCUMENTS

WO     WO-2025082455 A1 * 4/2025 ........... A61B 5/6889

OTHER PUBLICATIONS

Zhaoyang, "Time-Space Dimension Reduction of Millimeter-Wave Radar Point-Clouds for Smart-Home Hand-Gesture Recognition", Mar. 3, 2022, IEEE, 4425-4437 (Year: 2022).*

* cited by examiner

*Primary Examiner* — Renan Luque
(74) *Attorney, Agent, or Firm* — Birchwood IP

(57)     ABSTRACT

This invention pertains to lamp control and sleep monitoring using biometric data. The method includes several steps: first, using millimeter wave radar to obtain the point cloud height of center of gravity for azimuth data points; next, evaluating whether the detected movement qualifies as a half getting-up action; subsequently determining if it is a full getting-up action; and finally, controlling the lamp accordingly—if a half getting-up action is detected, the lamp operates in a first state, and if a full getting-up action is detected, in a second state. This approach links lamp operation to the user's physical actions, enhancing functionality and user experience.

9 Claims, 13 Drawing Sheets

| Sleep Quality Scoring Standards | | | | | |
|---|---|---|---|---|---|
| | Scoring item | Total score | Scoring standards | Score | Remarks |
| 1 | Total sleep duration T1 | 30（30~40） | When the sleep time is within the range of 7-9 hours, it is considered the best and the score is higher; the further away from this time range, the lower the score; an important indicator that affects the final evaluation of sleep quality; | | The current sleep model will flexibly allocate the proportion of various scores based on different sleep stages, adjust the weights, and finally output the total score |
| 2 | Light sleep duration T2 | 10(10~20) | When the total sleep duration reaches 7-9 hours, the proportion of light sleep duration to total sleep duration is in the high-quality range of 50%-70%. When the total sleep duration does not meet the basic requirements, the score will be based on the proportion of light sleep duration to total sleep duration, the higher the proportion, the higher the score; | | |
| 3 | Deep sleep duration T3 | 20(20~30) | The deep sleep duration is the highest weighted indicator in the entire sleep stage, and the higher the proportion in the total sleep duration, the higher the score; | | |
| 4 | Getting-up frequency C1 | 10(0~10) | The more the getting-up frequency during the sleep process, the lower the score; | | |
| 5 | Breathing quality B1 | 20(15~20) | For an entire sleep period, an average breathing frequency range of 12-16 is considered a high-quality range, and the further away from this breathing range, the lower the score; | | |
| 6 | flipping-over frequency F1 | 10(5~10) | For an entire night of sleep, the lower the flipping-over frequency, the higher the score; | | |
| Total score | | | | | |

FIG. 2

| Corresponding score | | | |
|---|---|---|---|
| Score ranking | Score range | Evaluation | |
| 1 | ≥95 | Sleep excellent | |
| 2 | ≥85 | Sleep good | |
| 3 | ≥60 | Sleep moderate | |
| 4 | <60 | Sleep poor | |

FIG. 3

LAMP CONTROL METHOD, SLEEP MONITORING METHOD AND DEVICE BASED ON BIOMETRIC DATA

CROSS-REFERENCE TO RELATED APPLICATIONS

This application claims priority of Chinese Patent Application No. 202410377167.3, filed on Mar. 29, 2024, the entire contents of which are incorporated herein by reference.

TECHNICAL FIELD

The present invention relates to the technical field of lamp control and sleep monitoring, and in particular to a lamp control method, a sleep monitoring method, a device, and a system based on biometric data.

BACKGROUND

The main function of sleep monitoring is to record the sleep state, breathing frequency and heartbeat, in order to improve the sleep quality. Early sleep monitoring products mainly used a contact based (wearable) method to measure the user's sign status during sleep, such as wristbands, watches, sleep bands, sleep pads, electrocardiogram monitors, cameras. The output results included vital sign parameters such as electroencephalogram, electrocardiogram, electromyography, average breathing frequency, and oxygen saturation. Based on the above test results, the sleep state was calculated comprehensively, and wearing wearable devices can affect the user's sleep comfort.

In recent two years, millimeter wave radar sleep monitoring devices have comprehensively determined and output sleep results by detecting parameters such as breathing, heart rate, and movement amplitude through receiving and transmission of electromagnetic waves. The sleep quality evaluation method, equipment, system, and medium based on millimeter wave radar, as disclosed in the Chinese invention patent (hereinafter referred to as Document 1) with the publication number CN115778352A, is based on the real vital biometric data of the subject. The sleep quality of the subject is evaluated based on three dimensions: in-bed/off-bed state, human body movements, and breathing cycle stability during nighttime sleep, which can objectively reflect the sleep quality of the subject. And the sleep monitoring device, method, and medium based on millimeter wave radar, as disclosed in the Chinese invention patent application (hereinafter referred to as Document 2) with the publication number CN112806975A, can obtain the heartbeat and average breathing frequency of the current target human body through analysis of the target echo data, and then determine the sleep state.

However, Document 1 and Document 2 still have the following problems: single functionality and low user experience.

SUMMARY

In response to The purpose of the present invention is to provide a lamp control method, device and system based on biometric data on account of the disadvantages of the prior art, aiming at increasing the functionality of the sleep monitoring device, and improving user experience.

The present invention achieves the above purpose through the following technical solution: a lamp control method based on biometric data, comprising the following steps:

a getting-up monitoring step: obtaining a point cloud height of center of gravity of each point in point cloud azimuth data detected by a millimeter wave radar;

a half getting-up evaluation step: determining whether the number of points with a preset height threshold of center of gravity triggered by point cloud height of center of gravity within a first set time exceeds a preset half getting-up threshold, if so, determining it as a half getting-up action;

a full getting-up evaluation step: determining whether the number of points with a preset height threshold of center of gravity triggered by point cloud height of center of gravity within a second set time exceeds a preset full getting-up threshold, if yes, determining it as a full getting-up action; and a first lamp control step: if a subject has a half getting-up action, controlling the lamp to work in a first state, and if a subject has a full getting-up action, controlling the lamp to work in the second state.

As a further solution of the present invention, the full getting-up evaluation step comprises: determining whether it is a half getting-up action in the half getting-up evaluation step, if yes, determining whether the number of points with a preset height threshold of center of gravity triggered by point cloud height of center of gravity within a second set time exceeds a preset full getting-up threshold, if yes, determining it as a full getting-up action.

As a further solution of the present invention, further comprising before the getting-up monitoring step:

a detection step: obtaining biometric data generated by reflected waves of a millimeter wave radar, the biometric data including point cloud azimuth data and a subject's energy intensity;

an in-bed evaluation step: analyzing an average breathing frequency based on the subject's energy intensity, and determining whether the average breathing frequency triggers a preset in-bed breathing threshold, if yes, determining whether the subject is within a preset detection boundary, if yes, determining it as the in-bed state;

an off-bed evaluation step: determining whether the subject has left the preset detection boundary, if yes, determining whether the radar has detected the subject's energy intensity, if not, starting to accumulate the time the subject has left the detection boundary; if the accumulated time triggers the preset off-bed duration threshold, determining it as the off-bed state; and a getting-up monitoring step: determining whether it is in an in-bed state in the in-bed evaluation step, if so, monitoring the point cloud height of center of gravity of each point in point cloud azimuth data detected by a millimeter wave radar in real time.

As a further solution of the present invention, further comprising the following step:

a gesture wake-up step: detecting point cloud azimuth data and velocity values based on electromagnetic wave signal reflection in real time, determining whether the point cloud orientation data triggers a preset gesture threshold, if so, determining whether the velocity value triggers the preset gesture velocity threshold, if so, controlling the lamp to turn on.

As a further solution of the present invention, further comprising after the detection step:

a someone presence evaluation step: determining whether to meet a preset someone determination condition through point cloud azimuth data detected by the millimeter wave radar and motion intensity based on energy intensity, if so, determining it as a someone state;

an approaching evaluation step: determining whether to meet a preset approaching determination condition through motion intensity and point cloud azimuth data detected by the millimeter wave radar, if so, determining it as an approaching action;

a second lamp control step: the lamp including a clock lamp and a main lamp; determining whether it is in the someone presence state in the someone presence evaluation step, if yes, controlling the clock lamp to turn on; determining whether it is an approaching action in the approaching evaluation step, and if yes, controlling the main lamp to turn on; determining whether it is in the off-bed state in the off-bed evaluation step, if yes, turning off the lamp; determining whether it is in the in-bed state in the in-bed evaluation step, if yes, turning off the lamp;

further comprising between the someone presence evaluation step and the half getting-up evaluation step: and a motion sign analysis step: dividing the detected real-time energy intensity into N parts and determining whether the energy intensity is only related to breathing and/or heartbeat motion intensity, if so, assigning a value of 1 to the motion sign parameter, if no, associating the motion sign parameter with the motion intensity, with a value range of 2 to N;

further comprising after the motion sign analysis step:

a walking-around evaluation step: determining whether the motion sign parameter in the motion sign analysis step is 1, if yes, associating the motion sign parameter with the motion intensity, and determining whether the motion sign parameter triggers a preset walking-around threshold, if yes, determining it as a walking-around action, and turning on the main lamp.

As a further solution of the present invention, further comprising after the someone presence evaluation step:

a voice activation step: determining whether it is in the someone state in the someone presence evaluation step, if yes, activating a voice device;

further comprising after the voice activation step and the motion sign analysis step:

a struggling evaluation step: determining whether the motion sign parameter in the motion sign analysis step is 1, if yes, associating the motion sign parameter with the motion intensity, and determining whether the motion sign parameter triggers a preset struggling threshold, if yes, determining it as a struggling action;

an inquiry wake-up step: determining whether it is determined as a struggling action in the struggling evaluation step, if yes, the voice device will emit a preset inquiry voice;

a getting-up prompt step: determining whether it is in the full getting-up state in the full getting-up evaluation step, if yes, the voice device will emit a safety voice;

an early warning step: determining whether there is a response to the inquiry voice, if no, repeating the inquiry wake-up step; and an alarm step: determining whether the inquiry wake-up step is repeated no less than 2 times, if yes, reporting the alarm information to a server.

The present invention also provides another technical solution: a sleep monitoring method, controlling a lamp using the lamp control method based on biometric data according to any of the preceding items, the sleep monitoring method further comprises the following steps:

a preset step: presetting at least two deep sleep duration value ranges, at least two light sleep duration value ranges, at least two getting-up frequency value ranges, at least two average breathing frequency value ranges, and at least two flipping-over frequency value ranges, and assigning corresponding scores to each value range;

a value acquisition step: calculating the deep sleep duration value, light sleep duration value, getting-up frequency value, average breathing frequency value, and flipping-over frequency value based on the biometric data collected by the millimeter wave radar;

a scoring step: mapping the deep sleep duration value to the deep sleep duration value range, and obtaining the deep sleep rating value; mapping the light sleep duration value to the light sleep duration value range, and obtaining the light sleep score value; mapping the getting-up frequency value to the getting-up frequency value range, and obtaining the getting-up score value; mapping the average breathing frequency value to the average breathing frequency value range, and obtaining the breathing score value; mapping the flipping-over frequency value to the flipping-over frequency value range, and obtaining the flipping-over score value; and an overall evaluation step: adding the deep sleep score value, light sleep score value, getting-up score value, breathing score value, and turning-over score value to obtain the total sleep score.

As a further solution of the present invention, further comprising between the detection step and the value acquisition step:

a sleep state evaluation step: determining whether it is in the in-bed state in the in-bed evaluation step, if yes, performing a sleep state determination every a predetermined time period, the sleep state including a waking state, a light sleep state, and a deep sleep state, and obtaining the deep sleep duration value and the light sleep duration value;

a flipping-over evaluation step: determining whether to be determined as the in-bed state in the in-bed evaluation step, if yes, monitoring point cloud azimuth data detected by the millimeter wave radar and motion intensity based on energy intensity in real time, and determining whether the motion intensity is enough to trigger the preset turning-over threshold, if yes, determining whether the point cloud azimuth data is enough to trigger the preset point cloud change threshold, if yes, determining it as a turning-over action and recording the flipping-over frequency;

a physiological parameter analysis step: screening out an energy range that matches the real breathing change based on the analysis of real-time energy intensity detected by the millimeter wave radar, and converting the frequency to obtain the breathing rate; and a value acquisition step: obtaining the deep sleep duration value and the light sleep duration value based on the sleep state evaluation step, obtaining the getting-up frequency value based on the off-bed evaluation step, obtaining the average breathing frequency value based on the physiological parameter analysis step, and obtaining the flipping-over frequency value based on the flipping-over evaluation step.

The present invention also provides yet a technical solution: a lamp control device based on biometric data, comprising:

a detection module: used for obtaining point cloud azimuth data generated by reflected waves of a millimeter wave radar and a subject's biometric data;

an in-bed evaluation module: used for analyzing an average breathing frequency based on the subject's energy intensity, and determining whether the average breathing frequency triggers a preset in-bed breathing threshold, if yes, determining whether the subject is within a preset detection boundary, if yes, determining it as the in-bed state;

an off-bed evaluation module: used for determining whether the subject has left the preset detection boundary, if yes, determining whether the radar has detected the subject's energy intensity, if not, starting to accumulate the time the subject has left the detection boundary; if the accumulated time triggers the preset off-bed duration threshold, determining it as the off-bed state;

a getting-up monitoring module: used for determining whether it is in an in-bed state in the in-bed evaluation step, if yes, monitoring the point cloud height of center of gravity of each point in point cloud azimuth data detected by a millimeter wave radar in real time;

a half getting-up evaluation module: used for determining whether the number of points with a preset height threshold of center of gravity triggered by point cloud height of center of gravity within a first set time exceeds a preset half getting-up threshold, if yes, determining it as a half getting-up action;

a full getting-up evaluation module: determining whether the number of points with a preset height threshold of center of gravity triggered by point cloud height of center of gravity within a second set time exceeds a preset full getting-up threshold, if yes, determining it as a full getting-up action; and a first lamp control module: used for, if a subject has a half getting-up action, controlling the lamp to work in a first state; if a subject has a full getting-up action, controlling the lamp to work in the second state.

The present invention also provides yet another technical solution: a sleep monitoring system, comprising:

a millimeter wave radar monitoring module, used for emitting millimeter waves and receiving reflected waves, and generating detection data;

a master control MCU, communicated with the millimeter wave radar monitoring module, used for receiving and analyzing the detection data;

a voice module, communicated or electrically connected with the master control MCU; and a lighting module, communicated or electrically connected with the master control MCU;

wherein, the master control MCU controls the lighting module using the lamp control method based on biometric data according to any of the preceding items.

The beneficial effects of the present invention are as follows:

This solution correspondingly identifies the subject's half getting-up action (possibly getting up) and full getting-up action (confirmed getting up) through the half getting-up evaluation step and the full getting-up evaluation step, and the half getting-up action matches the first state of the lamp, while the full getting-up action matches the second state of the lamp to achieve the complete night lighting function. The first state and the second state can be set to different brightness or different lamp effects, so that the lamp is linked with the user's biometric action, and added to the sleep monitoring device, in order to realize diverse functions and improve user experience. When set to different brightness, it can adaptively light, save energy and protect the environment, intelligently adjust brightness instead of always maintaining full brightness or full darkness. At the same time, it also provides a comfortable lighting environment, avoiding injuries to the human eyes caused by sudden strong light, without the need to operate switches or grope in the dark, thereby reducing the risk of accidents such as falling.

BRIEF DESCRIPTION OF THE DRAWINGS

FIG. 2 is a schematic diagram of the sleep monitoring method and sleep monitoring system of the present invention for generating sleep quality scoring reports.

FIG. 3 is a schematic diagram of sleep evaluation based on the sleep quality scoring report in FIG. 2.

DETAILED DESCRIPTION OF THE PREFERRED EMBODIMENTS

Technical solutions in the embodiments of the present invention will be described clearly and completely in combination with figures in the embodiments of the invention. Obviously, the described embodiments are only part, but not all, of the embodiments of the invention. All other embodiments obtained by those of ordinary skill in the art without creative work based on the embodiments of the present invention are within the scope of protection of the present invention.

As shown in FIGS. 1-15, the embodiments of the present invention provide a lamp control method based on biometric data, comprising the following steps: a getting-up monitoring step, a half getting-up evaluation step, a full getting-up evaluation step and a first lamp control step. Wherein:

a getting-up monitoring step: obtaining a point cloud height of center of gravity of each point in point cloud azimuth data detected by a millimeter wave radar;

a half getting-up evaluation step: determining whether the number of points with a preset height threshold of center of gravity triggered by point cloud height of center of gravity within a first set time exceeds a preset half getting-up threshold, if so, determining it as a half getting-up action;

a full getting-up evaluation step: determining whether the number of points with a preset height threshold of center of gravity triggered by point cloud height of center of gravity within a second set time exceeds a preset full getting-up threshold, if yes, determining it as a full getting-up action; and a first lamp control step: if a subject has a half getting-up action, controlling the lamp to work in a first state, and if a subject has a full getting-up action, controlling the lamp to work in the second state. Specifically, the first stage of getting up is half getting-up action (possibly getting up), and the second stage of getting up is full getting-up action (confirmed getting up). The first state and the second state can be set to different brightness or different lamp effects, for example, the lamp brightness in the half getting-up action is lower than that in the full getting-up action.

Figure 4:
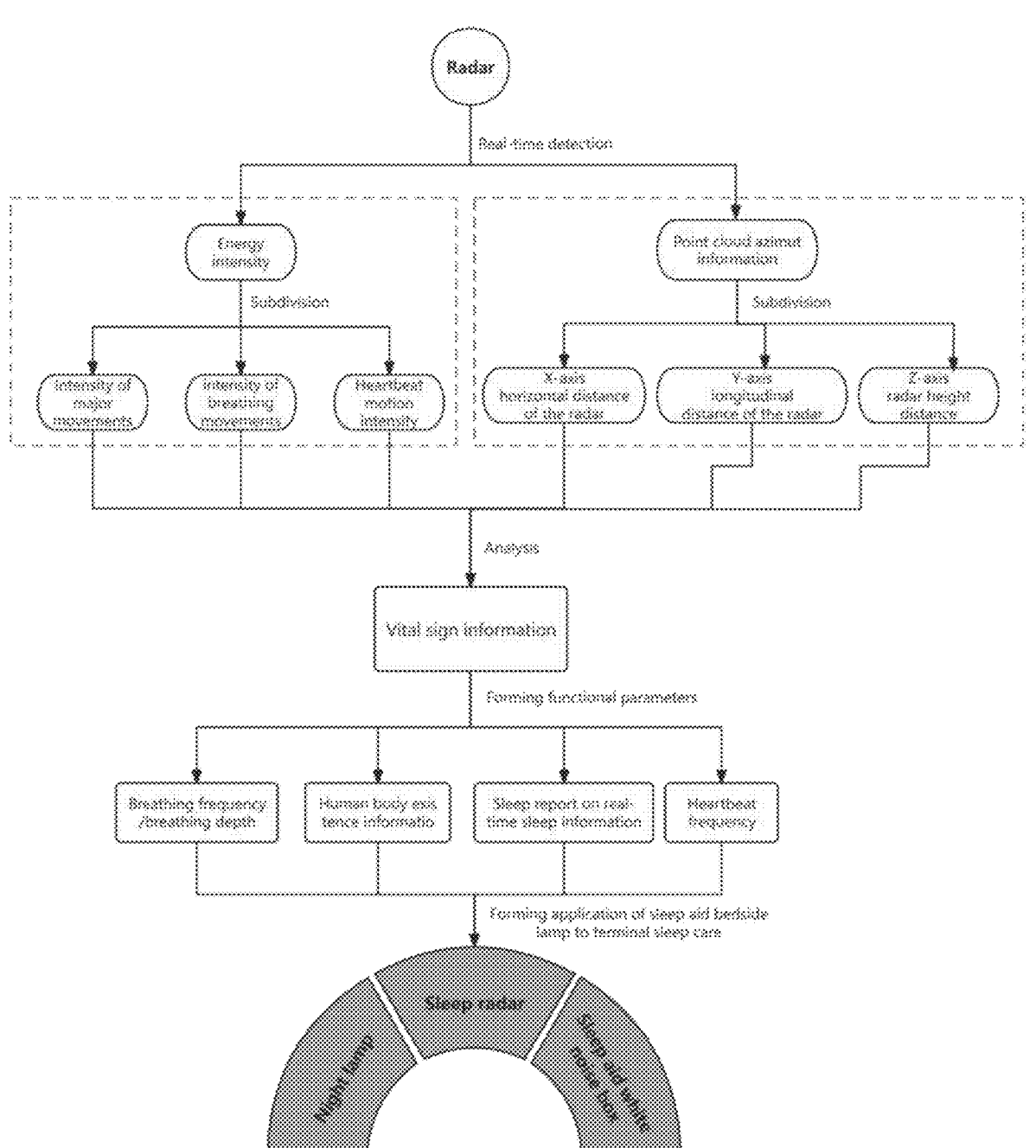
FIG. 4 is a flow block diagram of data detection and analysis of human body sign information by the millimeter wave radar of the present invention.
Figure 8:
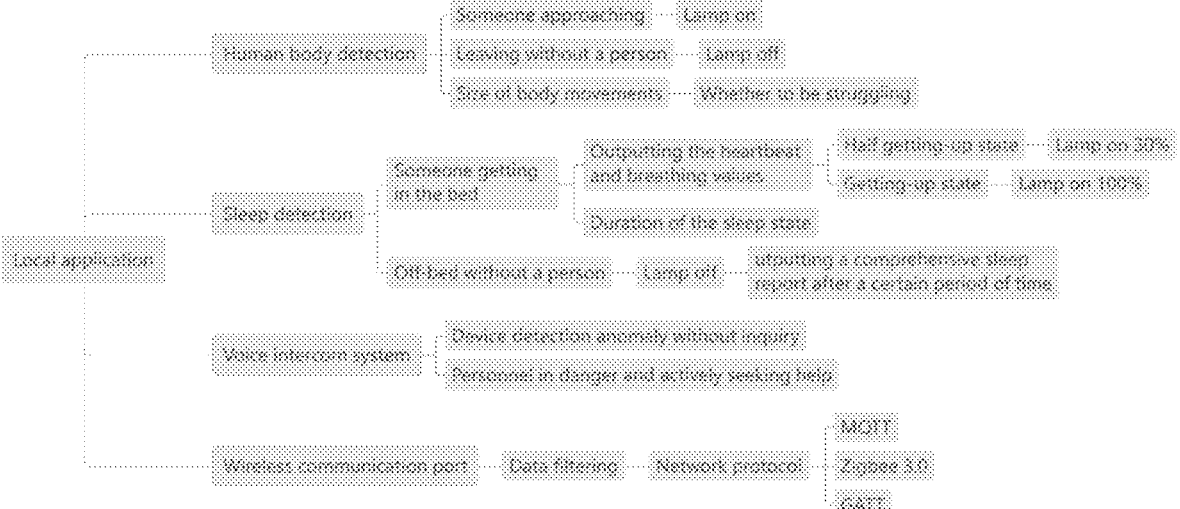
FIG. 8 is the overall flow block diagram of the present invention.
Figure 9:
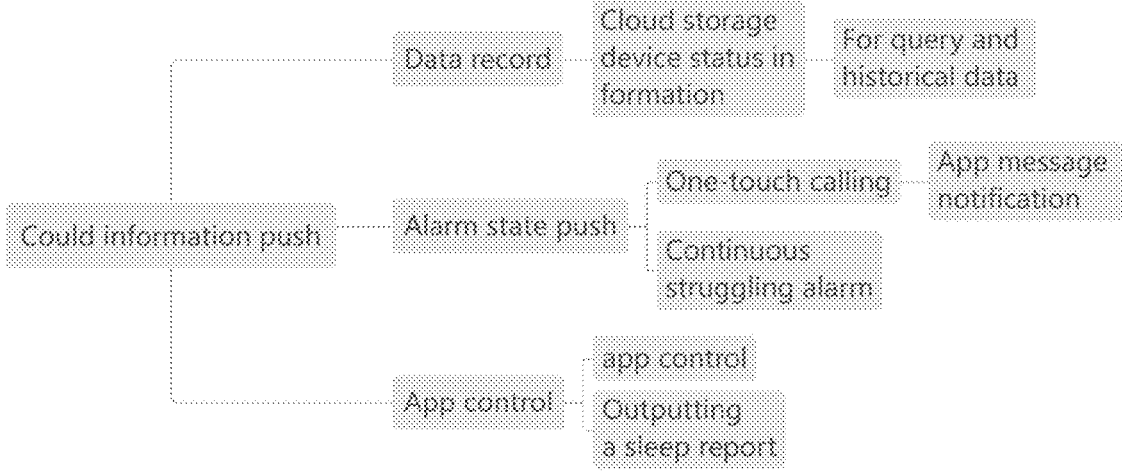
FIG. 9 is a flow block diagram of the cloud message push process of the present invention.
Figure 10:
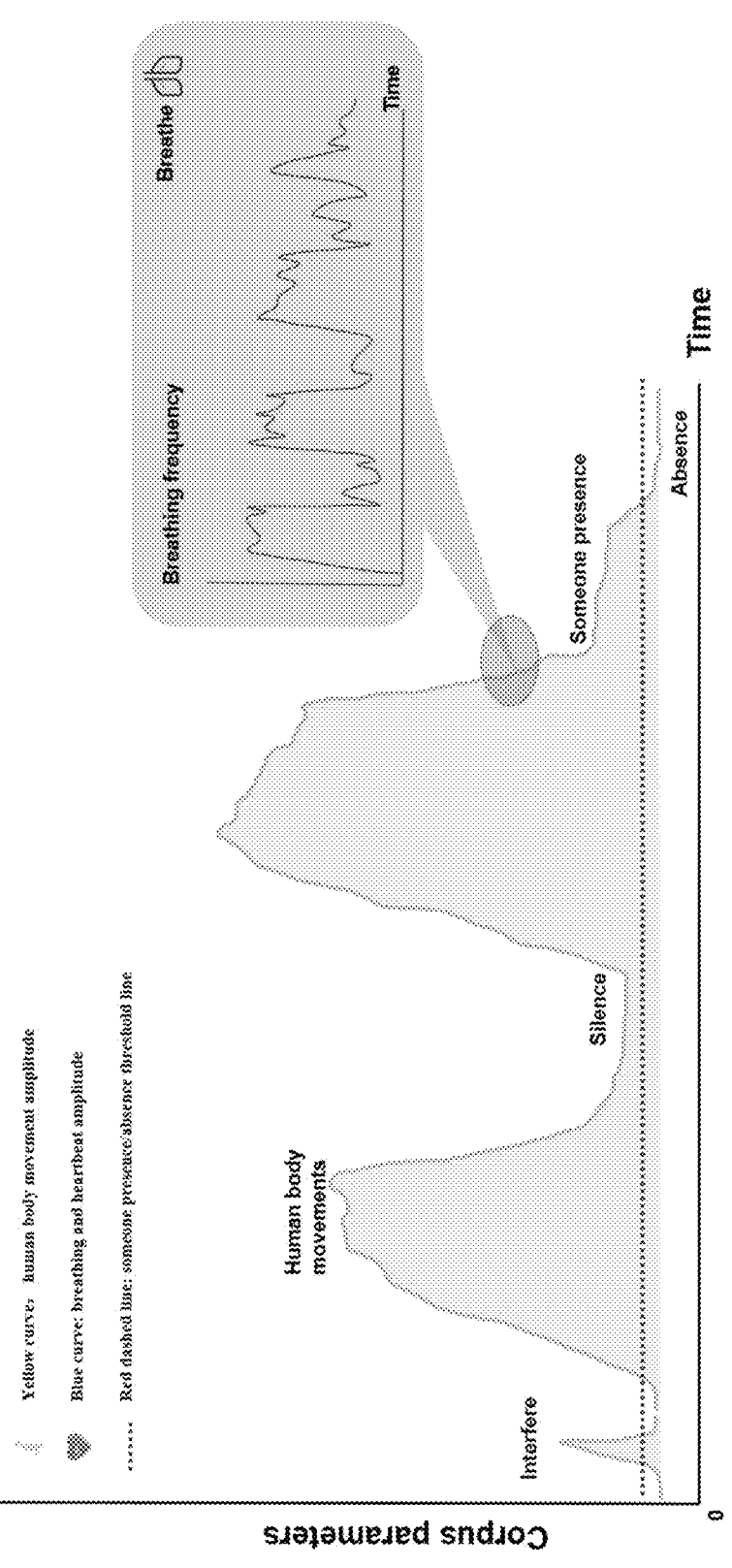
FIG. 10 is a waveform diagram of the biometric data detected by the millimeter wave radar of the present invention.

For example, as shown in FIG. 10, the radar has internal restrictions that only when entering the in-bed state, will the subsequent determination on getting up at night begin; in the in-bed state, the radar determines the current point cloud height of center of gravity in real time, and sets a height threshold of center of gravity through the previous model collection. In the actual determination process, if there are ≥3 points exceeding the threshold within 4 seconds, the first stage of getting up (possibly getting up) is reported. If the accumulated total number of points exceeding the threshold is ≥5 within the next 5 seconds, the second stage of getting up (confirmed getting up) is reported. As shown in FIGS. 4 and 8, the radar biometric action is linked with the lamp, and the linkage effect is achieved through the getting-up determination (possibly getting up/confirmed getting up) in the radar function. When a person sits up, the radar reports possible getting up, and the brightness of the linked night lamp is 30%, giving the person getting up at night a brightness adaptation process; when the person gets up completely, the radar reports confirmed getting up, and the brightness of the linked night lamp is 100%, achieving complete night lighting function.

This solution correspondingly identifies the subject's half getting-up action (possibly getting up) and full getting-up action (confirmed getting up) through the half getting-up evaluation step and the full getting-up evaluation step, and the half getting-up action matches the first state of the lamp, while the full getting-up action matches the second state of the lamp to achieve the complete night lighting function. The first state and the second state can be set to different brightness or different lamp effects, so that the lamp is linked with the user's biometric action, and added to the sleep monitoring device, in order to realize diverse functions and improve user experience. When set to different brightness, it can adaptively light, save energy and protect the environment, intelligently adjust brightness instead of always maintaining full brightness or full darkness. At the same time, it also provides a comfortable lighting environment, avoiding injuries to the human eyes caused by sudden strong light, without the need to operate switches or grope in the dark, thereby reducing the risk of accidents such as falling.

In an embodiment, as shown in FIGS. 4 and 8, the full getting-up evaluation step comprises: determining whether it is a half getting-up action in the half getting-up evaluation step, if yes, determining whether the number of points with a preset height threshold of center of gravity triggered by point cloud height of center of gravity within a second set time exceeds a preset full getting-up threshold, if yes, determining it as a full getting-up action. Specifically, the full getting-up evaluation step is performed after the half getting-up evaluation step. When a person sits up, the radar reports possible getting up, and the brightness of the lamp is 30%, giving the person getting up at night a brightness adaptation process; when the person gets up completely, the radar reports confirmed getting up, and the brightness of the lamp is 100%, achieving complete night lighting function.

In addition, after getting up is confirmed, the voice module can be controlled to emit a sound, such as buzz, to remind the elderly that they have already gotten up. Because most elderly people get up with dizziness and the possibility of falling, emitting a sound during getting up can serve as a good reminder.

Figure 6:
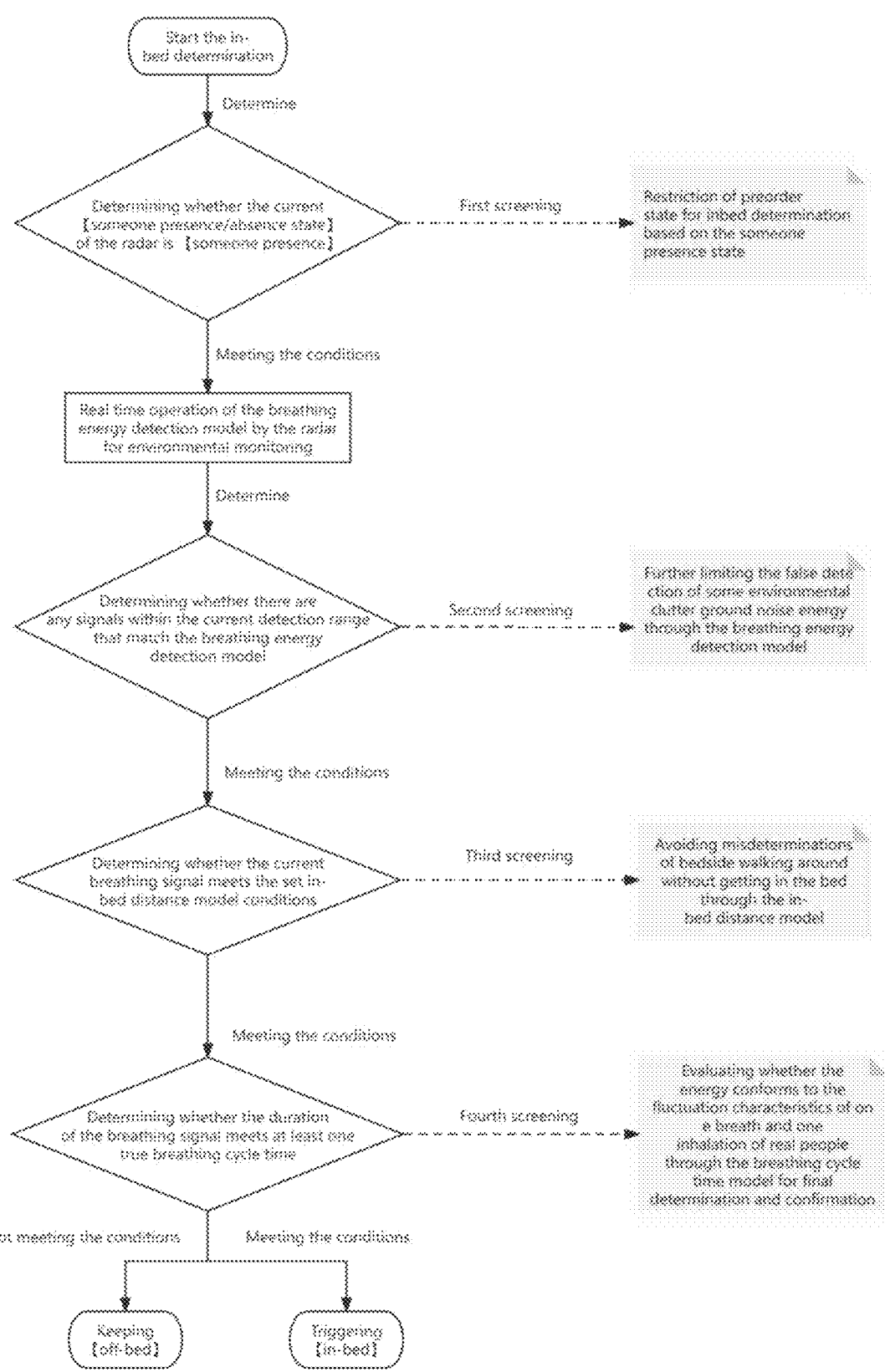
FIG. 6 is a flowchart of the in-bed evaluation step and the off-bed evaluation step of the present invention.

In another embodiment, further comprising before the getting-up monitoring step: a detection step, an in-bed evaluation step and an off-bed evaluation step. Wherein:

A detection step: obtaining biometric data generated by reflected waves of a millimeter wave radar, the biometric data including point cloud azimuth data and a subject's energy intensity; energy intensity includes intensities of major movements, breathing movements, and heartbeat movements;

An in-bed evaluation step: analyzing an average breathing frequency based on the subject's energy intensity, and determining whether the average breathing frequency triggers a preset in-bed breathing threshold, if yes, determining whether the subject is within a preset detection boundary, if yes, determining it as the in-bed state. For example, as shown in FIGS. 6 and 10, according to the installation method, the radar sets the in-bed detection boundary (just covering one bed position); when a person is lying on the bed, the millimeter wave radar detects a relatively stable intensity of breathing movements, and then compares the distance to confirm that the breathing intensity is within a reasonable in-bed range, the radar reports the in-bed state. The average breathing frequency can be analyzed by the millimeter wave radar based on the energy intensity detected in real time, and the intensity of breathing movements detected in real time can be screened to confirm the energy range that matches the intensity change of a real person's breathing, thereby converting the frequency to obtain the breathing rate. According to this algorithm, the accumulated breathing accuracy will gradually improve over time.

An off-bed evaluation step: determining whether the subject has left the preset detection boundary, if yes, determining whether the radar has detected the subject's energy intensity, if not, starting to accumulate the time the subject has left the detection boundary; if the accumulated time triggers the preset off-bed duration threshold, determining it as the off-bed state. For example, when a person leaves the set detection boundary and the radar cannot detect any energy of the body's intensities of major movements, breathing movements, and heartbeat movements, time accumulation begins. If the absence condition is met for 30 seconds, the off-bed state is output.

a getting-up monitoring step: determining whether it is in an in-bed state in the in-bed evaluation step, if so, monitoring the point cloud height of center of gravity of each point in point cloud azimuth data detected by a millimeter wave radar in real time.

Figure 11:
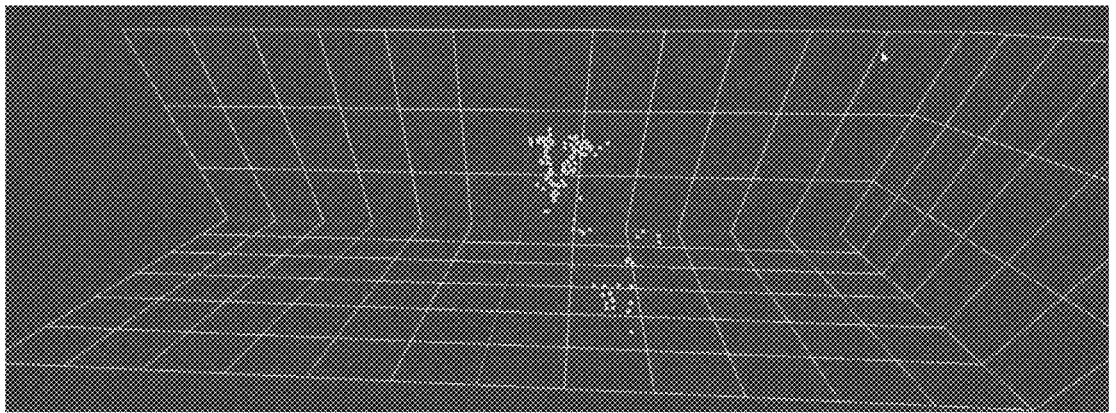
FIG. 11 is a schematic diagram of the point cloud orientation of the gesture wake-up step of the present invention.

In yet another embodiment, as shown in FIGS. 4 and 11, the lamp control method based on biometric data further comprises the following steps:

A gesture wake-up step: detecting point cloud azimuth data and angle and velocity values of electromagnetic wave signal reflection by the millimeter wave radar in real time, obtaining the energy intensity and velocity values reflected by moving objects through changes in electromagnetic wave frequency and angle, determining whether the point cloud orientation data triggers a preset gesture threshold, if yes, determining whether the velocity value triggers the preset gesture velocity threshold, if yes, controlling the lamp to turn on. The gesture threshold comprises a gesture direction threshold or a gesture azimuth threshold, such as waving left hand, waving right hand, continuously waving a hand, clamping hands twice. Energy intensity or motion intensity can also be added as auxiliary determination conditions to trigger the gesture wake-up step, where the motion intensity includes the intensity of major movements. Preferably, the clock lamp is controlled to turn on. For example, as shown in FIG. 11, the millimeter wave radar detects the real-time changes in the distribution of point clouds and the value of velocity. If the velocity value is determined to reach the set threshold and the point cloud change amplitude is large enough to exceed the set gesture recognition value, a gesture command is reported. For example, if a person waves their hand at a device, the device will automatically light up the clock for time indication; or if a person waves their hand at a device, the device will flash lights, thereby improving the linkage between action and lamp effects.

Figure 5:
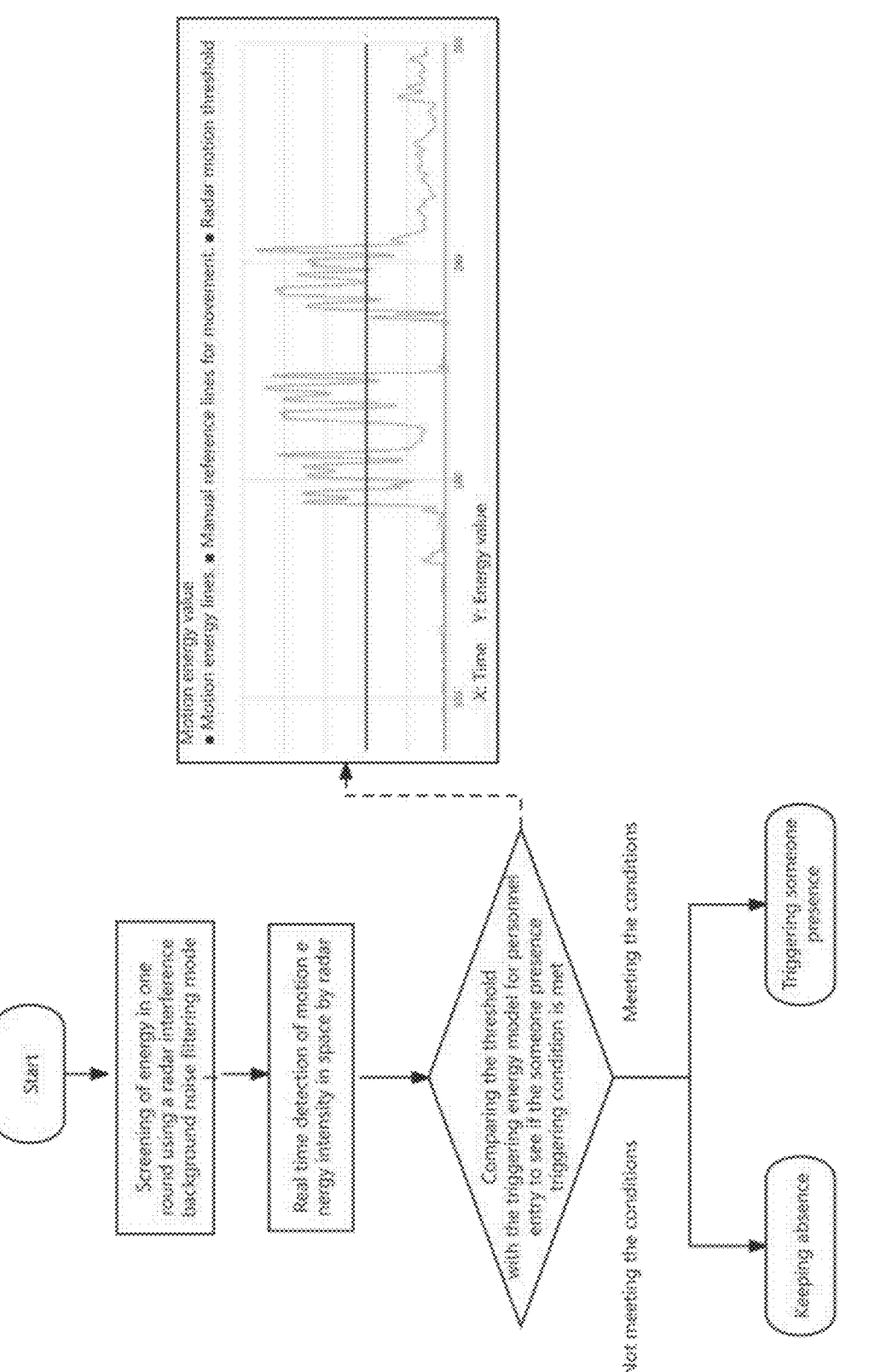
FIG. 5 is a flowchart and waveform diagram of the someone presence evaluation step of the present invention.

In a further embodiment, further comprising after the detection step: a someone presence evaluation step, an approaching evaluation step and a second lamp control step, and further comprising between the someone presence evaluation step and the half getting-up evaluation step: a motion sign analysis step. Further comprising after the motion sign analysis step: a walking-around evaluation step. Wherein:

A someone presence evaluation step: determining whether to meet a preset someone presence determination condition through point cloud azimuth data detected by the millimeter wave radar and motion intensity based on energy intensity, if yes, determining it as a someone presence state. Specifically, determining whether the motion intensity is enough to trigger the preset someone presence threshold is the preset velocity of movement, range of movement, and breathing frequency, if yes, determining whether the point cloud azimuth data triggers the preset distance boundary, if yes, determining it as the someone presence state. For example, as shown in FIG. 5, the millimeter wave radar detects entry of stronger motion intensity, accompanied by gradually approaching point cloud azimuth information, until the set distance boundary condition is triggered, and the radar reports the someone presence state. After someone presence is recorded, the someone presence/absence state every hour. If there is a continuous period of 2-3 hours, the device will report an abnormal state.

An approaching evaluation step: determining whether to meet a preset approaching determination condition through motion intensity and point cloud azimuth data detected by the millimeter wave radar, if yes, determining it as an approaching action. Specifically, the millimeter wave radar detects the motion intensity and point cloud azimuth data in real time, and calculates the time of receiving electromagnetic wave reflection. If the electromagnetic wave receiving time becomes shorter and there is a continuous change, it is determined as an approaching action.

A second lamp control step: the lamp including a clock lamp and a main lamp; determining whether it is in the someone presence state in the someone presence evaluation step, if yes, controlling the clock lamp to turn on; determining whether it is an approaching action in the approaching evaluation step, and if yes, controlling the main lamp to turn on; determining whether it is in the off-bed state in the off-bed evaluation step, if yes, turning off the lamp; determining whether it is in the in-bed state in the in-bed evaluation step, if yes, turning off the lamp. For example, when the millimeter wave radar detects the entry of a moving object and outputs the someone presence, the clock lamp will light up; if a person is detected approaching, the main lamp is turned on. If the radar detects a person getting in the bed, the lamp is gradually turned off. When the millimeter wave radar detects a getting-up action, the clock lamp is output; if someone is detected walking around, the main lamp is output.

A motion sign analysis step: dividing the detected real-time energy intensity into N parts and determining whether the energy intensity is only related to breathing and/or heartbeat motion intensity, if yes, assigning a value of 1 to the motion sign parameter, if no, associating the motion sign parameter with the motion intensity, with a value range of 2 to N, preferably N is 100. For example, the millimeter wave radar divides the energy intensity detected in real time into 100 parts. When only breathing/heartbeat intensity is detected as energy intensity, it is considered to be in a stationary state with a motion sign parameter of 1; when the detected energy intensity has an intensity of major movements, the motion sign parameter is associated with the motion intensity, with a range of 2-100. The larger the movement, the higher the motion sign parameter. For example, in motion sign parameters, the values for deep sleep are 1-3, for quietly playing with a phone are 5-10, for flipping over are 10-30, for coughing and struggling are 30-70, and for walking around are 70-100. Continuously monitor for 5 minutes and determining how many movements were made within that 5 minute period. Based on the recorded frequency, make a sleep score and an abnormal alarm.

A walking-around evaluation step: determining whether the motion sign parameter in the motion sign analysis step is 1, if yes, associating the motion sign parameter with the motion intensity, and determining whether the motion sign parameter triggers a preset walking-around threshold, if yes, determining it as a walking-around action, and turning on the main lamp. For example, in the motion sign parameters, the walking around motion is 70-100. If the walking around motion is detected, the main lamp will be turned on, further improving the linkage between the biometric action and the lamp.

the someone presence evaluation step: a voice activation step. Further comprising after the voice activation step and the motion sign analysis step: a struggling evaluation step, an inquiry wake-up step, a getting-up prompt step, an early warning step and an alarm step. Wherein:

A voice activation step: determining whether it is in the someone presence state in the someone presence evaluation step, if yes, activating a voice device. For example, the millimeter wave radar emits a someone presence signal. The device begins to work. The voice function of the device is activated. This product is triggered by offline voice. When the device is set to sound: turn on/off/somebody/help, the millimeter wave radar will trigger a remote APP push, making a remote distress alarm. Upon receipt of the voice trigger, a voice reply will be sent: lights on/off/guardian notified.

A struggling evaluation step: determining whether the motion sign parameter in the motion sign analysis step is 1, if yes, associating the motion sign parameter with the motion intensity, and determining whether the motion sign parameter triggers a preset struggling threshold, if yes, determining it as a struggling action. For example, in motion sign parameters, the struggling action is 30-70.

An inquiry wake-up step: determining whether it is determined as a struggling action in the struggling evaluation step, if yes, the voice device will emit a preset inquiry voice.

A getting-up prompt step: determining whether it is in the full getting-up state in the full getting-up evaluation step, if yes, the voice device will emit a safety voice. For example, when a person wakes up at night, they will automatically light up the clock and auxiliary lighting based on their getting-up actions, and prompt a safety voice. When a person walks around, lighting instructions will be provided, and the lamp will be turned off automatically after a person gets in the bed.

An early warning step: determining whether there is a response to the inquiry voice, if no, repeating the inquiry wake-up step.

an alarm step: determining whether the inquiry wake-up step is repeated no less than 2 times, if yes, reporting the alarm information to a server.

A sleep monitoring method, as shown in FIGS. 1-15, controls the lamp using the lamp control method based on biometric data according to any of the preceding items, and the sleep monitoring method further comprises the following steps: a preset step, a detection step, a someone presence evaluation step, an in-bed evaluation step, a getting-up monitoring step, a half getting-up evaluation step, a full getting-up evaluation step, a first lamp control step, a value acquisition step, a scoring step and an overall evaluation step. Wherein:

A preset step: as shown in FIG. 2, presetting at least two deep sleep duration value ranges, at least two light sleep duration value ranges, at least two getting-up frequency value ranges, at least two average breathing frequency value ranges, and at least two flipping-over frequency value ranges, and assigning corresponding deep sleep scores to the at least two deep sleep duration value ranges; assigning corresponding light sleep scores to the at least two light sleep duration value ranges, assigning corresponding getting-up scores to the at least two getting-up frequency value ranges, assigning corresponding breathing scores to the at least two average breathing frequency value ranges, and assigning corresponding flipping-over scores to the at least two flipping-over frequency value ranges. Specifically, the current sleep model will flexibly allocate the proportion of various scores based on different sleep stages, adjust the weights, and finally output the total score.

A detection step: obtaining biometric data generated by reflected waves of a millimeter wave radar, the biometric data including point cloud azimuth data and a subject's energy intensity; energy intensity includes intensities of major movements, breathing movements, and heartbeat movements.

A someone-existing evaluation step: determining whether to meet a preset someone presence determination condition through point cloud azimuth data detected by the millimeter wave radar and motion intensity based on energy intensity, if yes, determining it as a someone-existing state.

An in-bed evaluation step: analyzing an average breathing frequency based on the subject's energy intensity, and determining whether the average breathing frequency triggers a preset in-bed breathing threshold, if yes, determining whether the subject is within a preset detection boundary, if yes, determining it as the in-bed state.

A getting-up monitoring step: determining whether it is in an in-bed state in the in-bed evaluation step, if yes, monitoring the point cloud height of center of gravity of each point in point cloud azimuth data detected by a millimeter wave radar in real time.

A half getting-up evaluation step: determining whether the number of points with a preset height threshold of center of gravity triggered by point cloud height of center of gravity within a first set time exceeds a preset half getting-up threshold, if yes, determining it as a half getting-up action.

A full getting-up evaluation step: determining whether the number of points with a preset height threshold of center of gravity triggered by point cloud height of center of gravity within a second set time exceeds a preset full getting-up threshold, if yes, determining it as a full getting-up action.

a first lamp control step: if a subject has a half getting-up action, controlling the lamp to work in a first state, and if a subject has a full getting-up action, controlling the lamp to work in the second state.

A value acquisition step: calculating the deep sleep duration value, light sleep duration value, getting-up frequency value, average breathing frequency value, and flipping-over frequency value based on the biometric data collected by the millimeter wave radar.

A scoring step: mapping the deep sleep duration value to the deep sleep duration value range, and obtaining the deep sleep rating value; mapping the light sleep duration value to the light sleep duration value range, and obtaining the light sleep score value; mapping the getting-up frequency value to the getting-up frequency value range, and obtaining the getting-up score value; mapping the average breathing frequency value to the average breathing frequency value range, and obtaining the breathing score value; mapping the flipping-over frequency value to the flipping-over frequency value range, and obtaining the flipping-over score value.

An overall evaluation step: as shown in FIG. 2, adding the deep sleep score value, light sleep score value, getting-up score value, breathing score value, and flipping-over score value to obtain the total sleep score. Specifically, referring to FIG. 2, the current sleep model will flexibly allocate the proportion of various scores based on different sleep stages, adjust the weights, and finally output the total score.

In this sleep monitoring method, the preset step is used to divide the sleep duration value, getting-up frequency value, average breathing frequency value, and flipping-over frequency value into different value ranges, and different sleep score values are assigned according to different value ranges; then, through the detection step, the subject's biometric data collected by the millimeter wave radar is obtained, and the biometric data is calculated and analyzed using the existing method/algorithm according to the value acquisition step, thereby obtaining the sleep duration value, getting-up frequency value, average breathing frequency value and flipping-over frequency value; next, through the scoring step, which value range the values obtained in the detection step fall into the preset step is determined, and the corresponding score value is output according to the corresponding score to the value range; then, the various score values are added to obtain the total sleep score; the total sleep score value is then sent to the mobile APP in the form of a sleep report through the server, providing a more specific and intuitive reference for determining the subject's sleep quality, better reflecting the sleep quality, and providing reference information for improving sleep quality and health and safety.

In another embodiment, the preset step further comprises: at least two value ranges are preset for the total sleep duration, and assigned with corresponding total sleep duration scores. The value acquisition step further comprises: summing the deep sleep duration value and the light sleep duration value to obtain the total sleep duration value. The scoring step further comprises: mapping the total sleep duration value to the total sleep duration value range, and obtaining the total sleep score value. An overall evaluation step: as shown in FIG. 2, adding the total sleep score value, deep sleep score value, light sleep score value, getting-up score value, breathing score value, and flipping-over score value to obtain the total sleep score. Specifically, the introduction of the total sleep duration value range, total sleep duration value and total sleep score value enables the total sleep score to evaluate and reflect the sleep monitoring quality more accurately.

Figure 7:
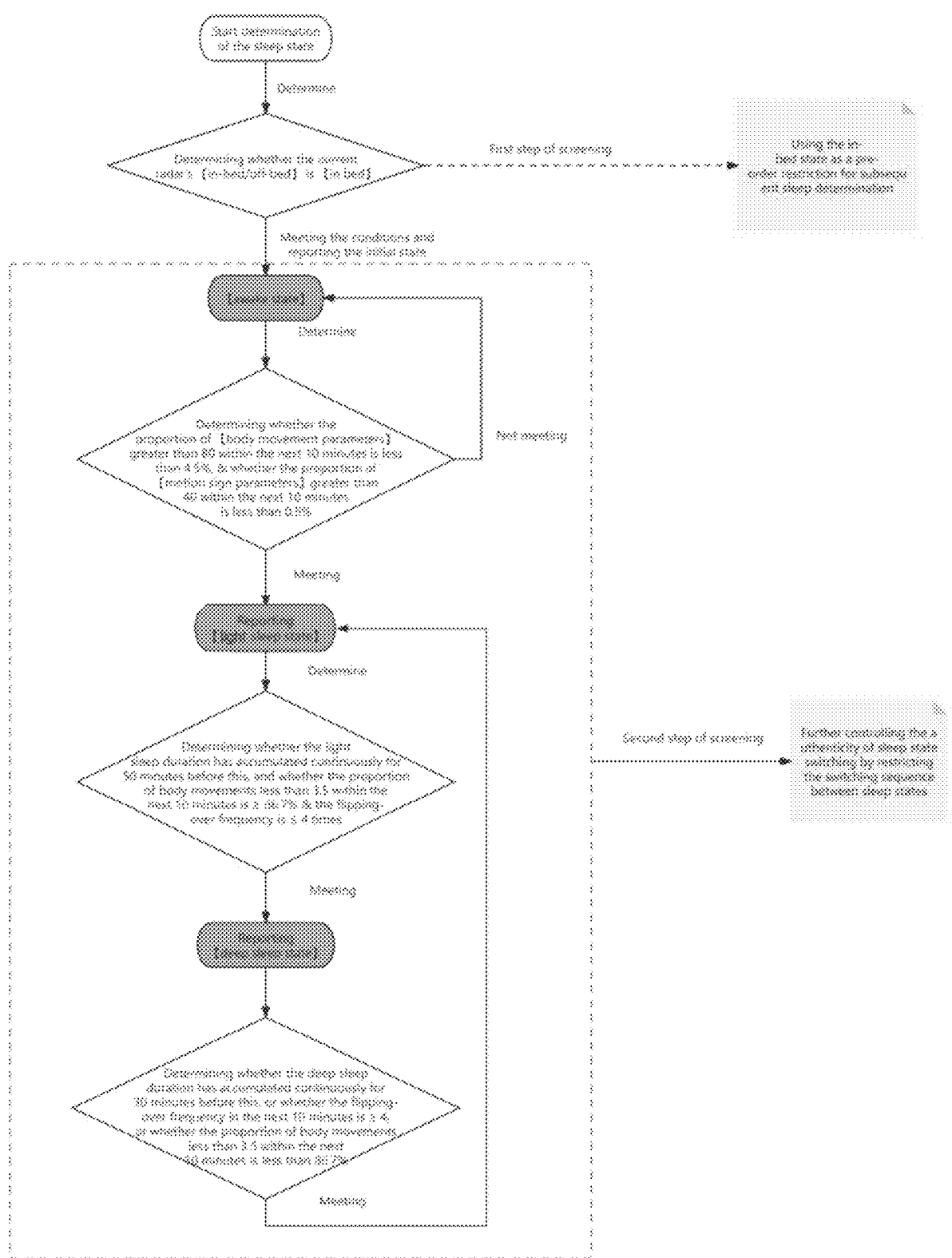
FIG. 7 is a flowchart of the sleep state determination in the sleep state evaluation step of the present invention.

In another embodiment, further comprising after the in-bed evaluation step: an off-bed evaluation step. Further comprising between the detection step and the value acquisition step: a sleep state evaluation step, a flipping-over evaluation step and a physiological parameter analysis step. Wherein:

An off-bed evaluation step: determining whether the subject has left the preset detection boundary, if yes, determining whether the radar has detected the subject's energy intensity, if not, starting to accumulate the time the subject has left the detection boundary; if the accumulated time triggers the preset off-bed duration threshold, determining it as the off-bed state and recording the off-bed frequency;

A sleep state evaluation step: determining whether it is in the in-bed state in the in-bed evaluation step, if yes, performing a sleep state determination every a predetermined time period, the sleep state including a waking state, a light sleep state, and a deep sleep state, and obtaining the deep sleep duration value and the light sleep duration value. For example, as shown in FIG. 7, the radar has made internal restrictions that only when entering the in-bed state, will the sleep state be comprehensively determined every 10 minutes in the future; and the order of changes in sleep state is limited to: awake ↔light sleep ↔deep sleep (there is no direct switching between awake and deep sleep states).

a flipping-over evaluation step: determining whether to be determined as the in-bed state in the in-bed evaluation step, if yes, monitoring point cloud azimuth data detected by the millimeter wave radar and motion intensity based on energy intensity in real time, and determining whether the motion intensity is enough to trigger the preset flipping-over threshold, if yes, determining whether the point cloud azimuth data is enough to trigger the preset point cloud change threshold, if yes, determining it as a flipping-over action and recording the flipping-over frequency. For example, after getting in the bed, the radar will detect the real-time movement momentum and point cloud distribution changes of the person lying in bed. If it is determined that the movement momentum reaches the threshold set for flipping over and the point cloud change amplitude is large enough to exceed the set value, the flipping-over frequency will be recorded. flipping-over frequency every 10 minutes is recorded, and the total frequency of ending a sleep is finally summarized. If flipping over is continued, an abnormal sleep alarm will be reported.

A physiological parameter analysis step: screening out an energy value or energy range that matches the real breathing change based on the analysis of real-time energy intensity detected by the millimeter wave radar, and converting the frequency to obtain the breathing rate. For example, the millimeter wave radar performs analysis based on the energy intensity detected in real time, and the breathing intensity detected in real time can be screened to confirm the energy range that matches the intensity change of a real person's breathing, thereby converting the frequency to obtain the breathing rate. According to this algorithm, the accumulated breathing accuracy will gradually improve over time. The millimeter wave radar calculates the amplitude of breathing by detecting a movement range of 0.5-10 mm, and measures the average value per unit time. The current average value is 10 seconds. If the breathing amplitude becomes relatively small, there will be a recorded pause in breathing. An energy range that matches the real heartbeat change is screened out based on the analysis of real-time energy intensity detected by the millimeter wave radar, and the frequency is converted to obtain the breathing rate; For example, the millimeter wave radar performs analysis based on the energy intensity detected in real time, and the heartbeat intensity detected in real time can be screened to confirm the energy range that matches the real heartbeat intensity change, thereby converting the frequency to obtain the heartbeat. According to this algorithm, the accumulated heartbeat accuracy will gradually improve over time.

a value acquisition step: obtaining the deep sleep duration value and the light sleep duration value based on the sleep state evaluation step, obtaining the getting-up frequency value based on the off-bed evaluation step, obtaining the average breathing frequency value based on the physiological parameter analysis step, and obtaining the flipping-over frequency value based on the flipping-over evaluation step.

In the sleep state evaluation step, the sleep state determination includes: awakeness determination, light sleep determination, and deep sleep determination. Wherein:

Light sleep determination: during the current predetermined time period, if the number of body movements is greater than the first threshold and the body movement index is less than the second threshold, or if the number of body movements is greater than the third threshold and the body movement index is less than the fourth threshold, it is determined from the waking state to the light sleep state; if the deep sleep duration value accumulates to a predetermined time, or if the flipping-over frequency during the current predetermined time period is greater than the fifth threshold, or if the number of body movements during the current predetermined time period is less than the sixth threshold and the body movement index is less than the seventh threshold, it is determined from the deep sleep state to the light sleep state. For example, as shown in FIG. 7, from the waking state to the light speed state, the former predetermined time period is 10 minutes, and the proportion of body movements greater than 8.0 within this 10-minute period is less than 4.5%, or the proportion of body movements greater than 40 within this 10-minute period is less than 0.5%. When entering the light sleep, the cumulative deep sleep duration is 30 minutes, or the flipping-over frequency within this 10-minute period is ≥4, or the proportion of body movements within this 10-minute period is less than 3.5, which is less than 86.7%.

Deep sleep determination: if the light sleep duration value accumulates for a predetermined time and the number of body movements during the current predetermined time period is less than the eighth threshold, the body movement index is not less than the ninth threshold, and the flipping-over frequency value is not greater than the tenth threshold, it is determined to be in a deep sleep state. For example, when entering the deep sleep from the light sleep, the cumulative light sleep duration is 50 minutes, and the proportion of body movements less than 3.5 within this 10-minute period is ≥86.7% and the flipping-over frequency is ≤4.

Awakening determination: determining whether it is in the in-bed state in the in-bed evaluation step, if yes, reporting the initial sleep state as the awake state; alternatively, if the conditions for deep sleep determination and light sleep determination are not met, it is determined to be in an awake state. For example, the initial sleep state upon getting in the bed is the awake state by default. Based on the above light and deep sleep states, if the conditions for light and deep sleep are not met, the awake state will be reported.

A lamp control device based on biometric data comprises a detection module, an in-bed evaluation module, an off-bed evaluation module, a getting-up monitoring module, a half getting-up evaluation module, a full getting-up evaluation module and a first lamp control module. Wherein:

a detection module: used for obtaining point cloud azimuth data generated by reflected waves of a millimeter wave radar and a subject's biometric data;

an in-bed evaluation module: used for analyzing an average breathing frequency based on the subject's energy intensity, and determining whether the average breathing frequency triggers a preset in-bed breathing threshold, if yes, determining whether the subject is within a preset detection boundary, if yes, determining it as the in-bed state;

an off-bed evaluation module: used for determining whether the subject has left the preset detection boundary, if yes, determining whether the radar has detected the subject's energy intensity, if not, starting to accumulate the time the subject has left the detection boundary; if the accumulated time triggers the preset off-bed duration threshold, determining it as the off-bed state;

a getting-up monitoring module: used for determining whether it is in an in-bed state in the in-bed evaluation step, if yes, monitoring the point cloud height of center of gravity of each point in point cloud azimuth data detected by a millimeter wave radar in real time;

a half getting-up evaluation module: used for determining whether the number of points with a preset height threshold of center of gravity triggered by point cloud height of center of gravity within a first set time exceeds a preset half getting-up threshold, if yes, determining it as a half getting-up action;

a full getting-up evaluation module: determining whether the number of points with a preset height threshold of center of gravity triggered by point cloud height of center of gravity within a second set time exceeds a preset full getting-up threshold, if yes, determining it as a full getting-up action; and The first lamp control module is used for, if a subject has a half getting-up action, controlling the lamp to work in a first state; if a subject has a full getting-up action, controlling the lamp to work in the second state;

The preset module is used for presetting at least two deep sleep duration value ranges, at least two light sleep duration value ranges, at least two getting-up frequency value ranges, at least two average breathing frequency value ranges, and at least two flipping-over frequency value ranges, and assigning corresponding deep sleep scores to the at least two deep sleep duration value ranges; assigning corresponding light sleep scores to the at least two light sleep duration value ranges, assigning corresponding getting-up scores to the at least two getting-up frequency value ranges, assigning corresponding breathing scores to the at least two average breathing frequency value ranges, and assigning corresponding flipping-over scores to the at least two flipping-over frequency value ranges.

The detection module is used for obtaining the subject's biometric data collected by the millimeter wave radar;

The value acquisition module is used for calculating the deep sleep duration value, light sleep duration value, getting-up frequency value, average breathing frequency value, and flipping-over frequency value based on the biometric data;

The scoring module is used for searching for the deep sleep duration value range containing the deep sleep duration value, and obtaining the deep sleep score value; searching for the light sleep duration value range containing the light sleep duration value, and obtaining the light sleep score value; searching for the getting-up frequency value range containing the getting-up frequency value, and obtaining the getting-up score value; searching for the average breathing frequency value range containing the average breathing frequency value, and obtaining the breathing score value; searching for the flipping-over frequency value range containing the flipping-over frequency value, and obtaining the flipping-over score value;

The overall evaluation module is used for adding the deep sleep score value, light sleep score value, getting-up score value, breathing score value, and flipping-over score value to obtain the total sleep score.

A sleep monitoring system comprises a millimeter wave radar monitoring module, a master control MCU, a voice module, a lighting module, a wireless communication module, a server and a mobile terminal. Wherein:

a millimeter wave radar monitoring module, used for emitting millimeter waves and receiving reflected waves, and generating detection data;

The master control MCU is communicated with the millimeter wave radar monitoring module, and used for receiving and analyzing the detection data, and performing the lamp control method based on biometric data according to any of the preceding items or performing the sleep monitoring method according to any of the preceding items;

The voice module is communicated or electrically connected with the master control MCU; the voice module includes a voice device;

the lighting module is communicated or electrically connected with the master control MCU; the lighting module includes a lamp, and the lamp includes a main lamp and a clock lamp;

The wireless communication module is communicated with the master control MCU, including a wireless module;

The server is communicated with the wireless communication module;

The mobile terminal is communicated with the server;

wherein, the master control MCU controls the lighting module using the lamp control method based on biometric data according to any of the preceding items. It is installed at the height within two meters above the bedside or on top of a room, toward the body part.

Figure 12:
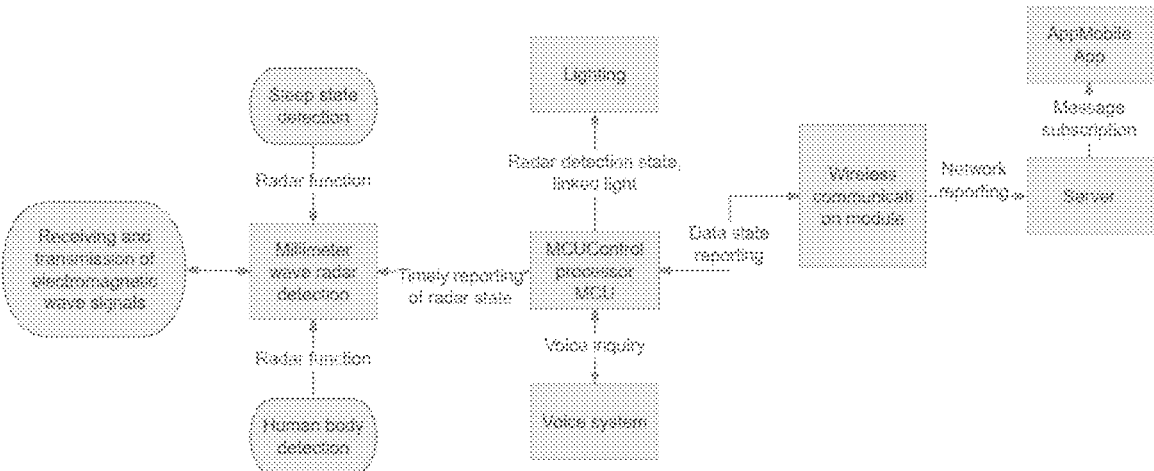
FIG. 12 is the overall block diagram of the sleep monitoring system of the present invention.
Figure 13:
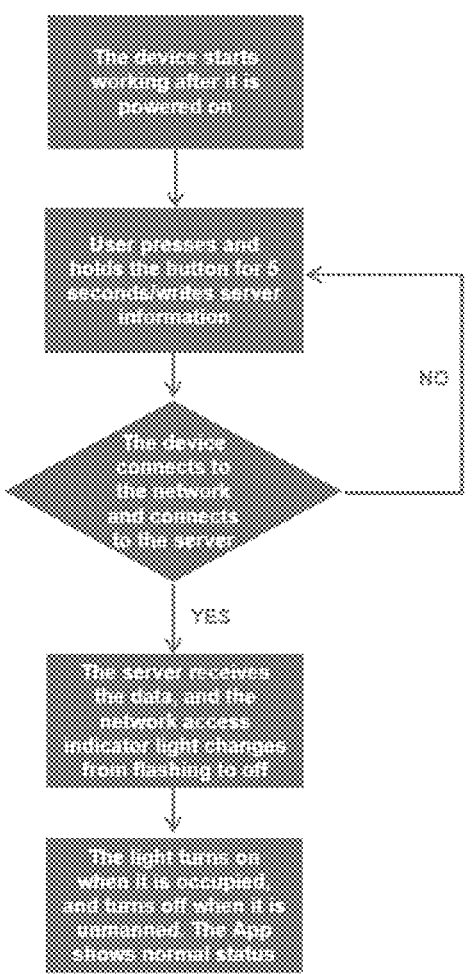
FIG. 13 is the power on flowchart of the sleep monitoring system of the present invention.
Figure 14:
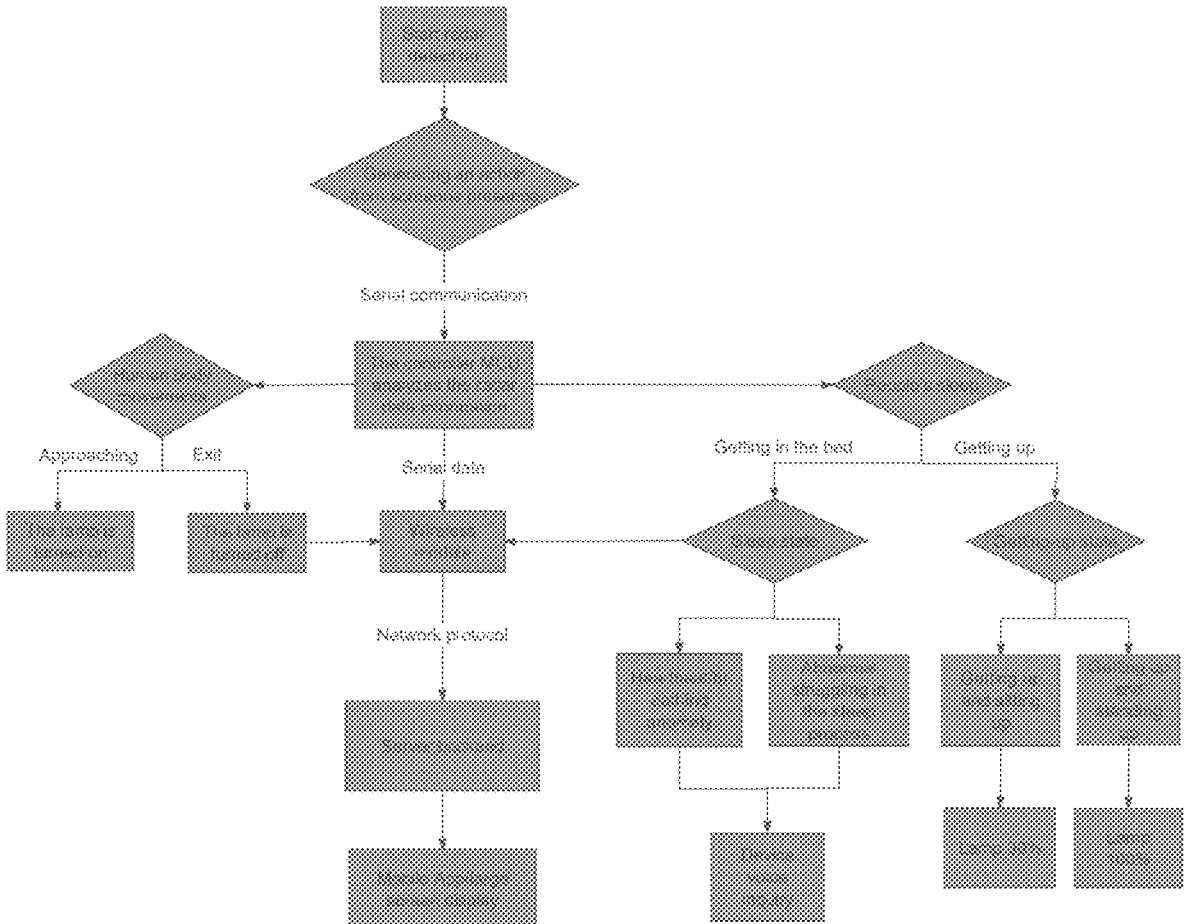
FIG. 14 is the overall flow block diagram of the sleep monitoring system of the present invention.
Figure 15:
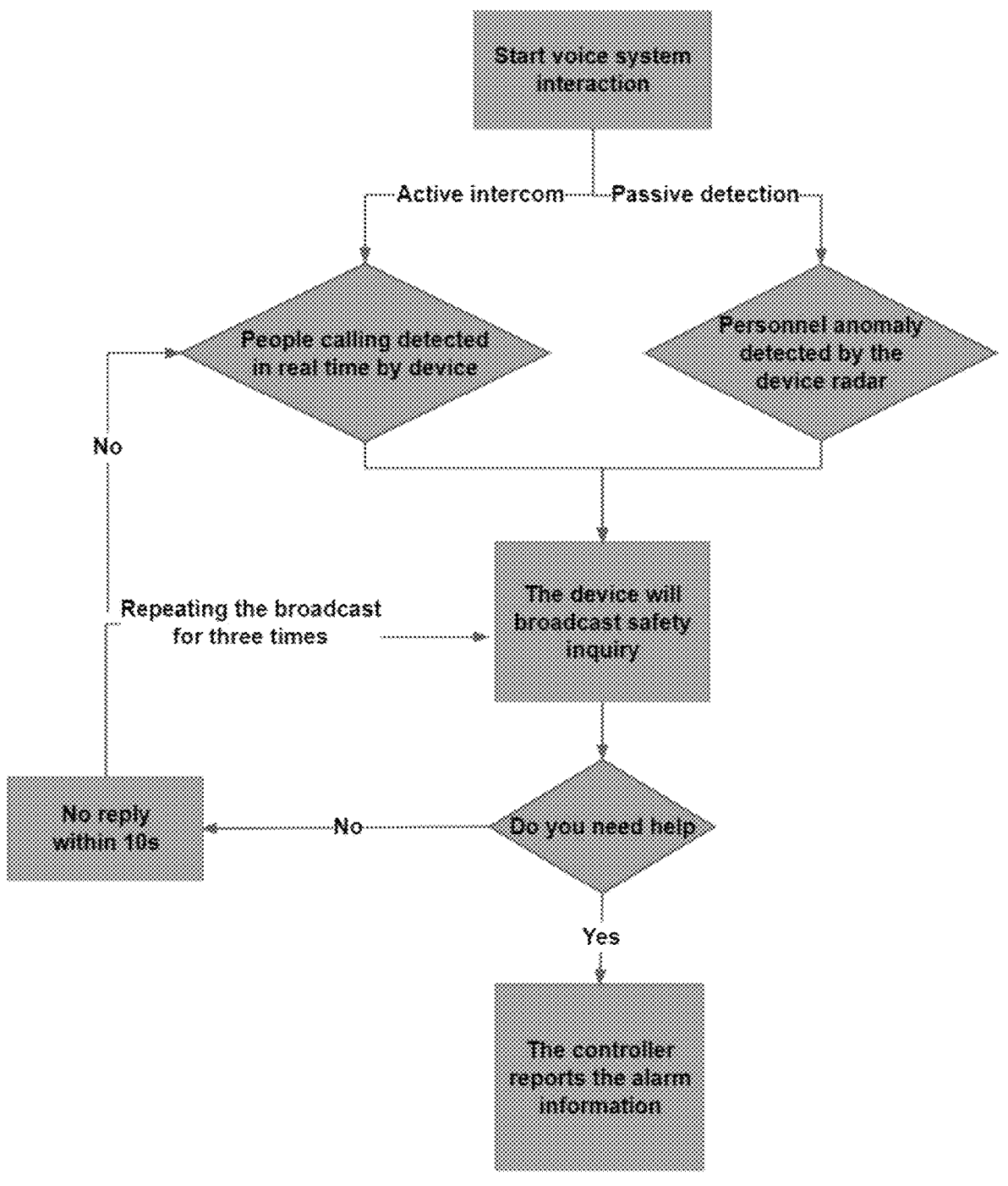
FIG. 15 is the workflow diagram of the voice module of the present invention.

As shown in FIG. 12, the millimeter wave radar monitoring module is connected with the server through the wireless communication module, and displays relevant subscription information on the mobile App or backend. As shown in FIG. 13, the power-on process is triggered by physical buttons until the device is connected to the server normally, and the LED light status and data of the device are reported normally. As shown in FIG. 14, the millimeter wave radar detects the presence and sleep process of the human body. The radar sends the detected information state to the controller MCU, which is the master control MCU, through a serial port connection. The MCU respectively analyzes the radar detection attribute status. When it belongs to the sleep state of the person getting in the bed, the MCU combines whether there are breathing and heartbeat abnormalities during the sleep process, whether there are abnormal struggles during the sleep process, and controls the voice system interaction to emit a safety inquiry. If there is a getting-up state, the MCU will also control the lamp to turn on, and the wireless module will report these states to the cloud server. The mobile App can subscribe to messages. As shown in FIG. 15, the sleep monitoring system supports the offline voice function, which can actively or passively engage in voice interaction. When people are in danger, they can directly shout for help through intercom. People can respond to voice inquiries. When people are detected to be breathing abnormally or struggling during sleep, the voice system will actively ask if they need help, and meanwhile reports an alarm message to the service center.

Specifically, the master control MCU will filter and process some information based on the human body existence information, sleep state information, and voice intercom information reported by the millimeter wave radar, and then transmit it to the cloud through the MQTT protocol. When a person approaches the device at a certain distance, the device light will turn on, or when someone gets up, the light will be gradually brightened; when a person moves a certain distance away from the device, the device lamp will turn off, or someone will leave the bed, while also recording the departure of the person. When a person approaches the bed, their breathing and heartbeat begin to count to evaluate whether they are in a stable sleep state. The deep/light sleep state is evaluated at intervals of 5-10 minutes, and the sleep duration is also recorded. After a certain sleep duration, a sleep quality report is output. While sleeping, local algorithms will determine the flipping-over and struggling states of people based on their body movement characteristics and promptly issue alarms. Cloud applications mainly rely on data status. After data filtering, the wireless module transmit the status of local applications to the cloud backend, and then display the data to users through the app. At the same time, users can also control and set functions of the device through the management backend and app. The wireless communication follows standard protocols MQTT, zigbee 3.0, and GATT, transmitting data to the backend for storage and recording, and performing real-time linkage based on importance. The main alarm states include one-touch calling, sleep struggle, voice call, etc., which can be customized through some cloud services to achieve app message push, SMS push, or phone notification. The backend can also be associated with guardians. The mobile terminal App can set the functions of the device and view real-time alarm information and historical records, or set the sleep time period according to the user's sleep habits. On the page, different sleep quality reports in different phases can be compared.

Figure 1:
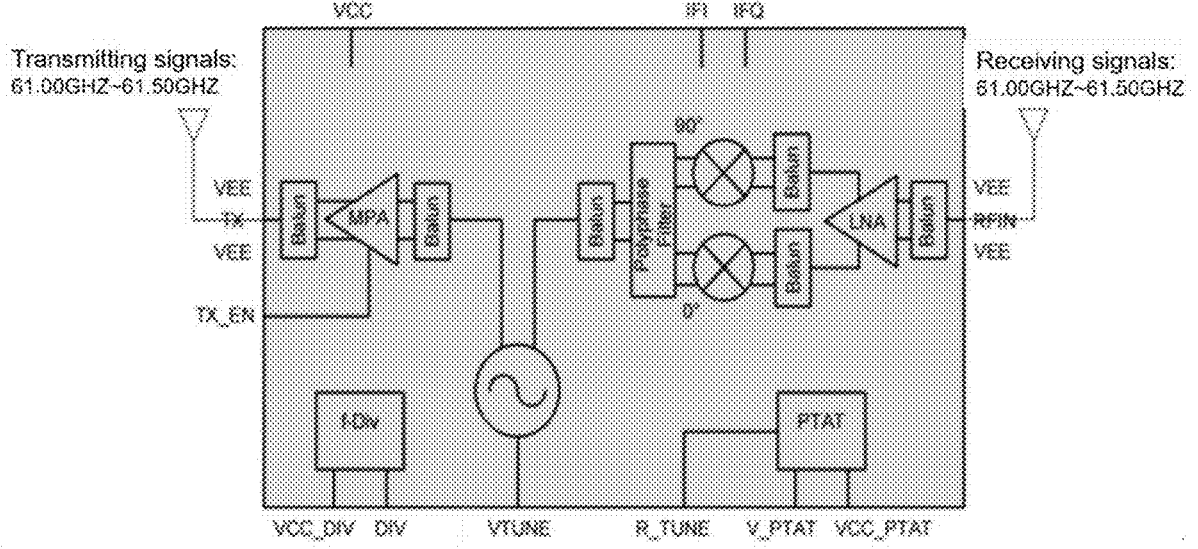
FIG. 1 is a schematic block diagram of the millimeter wave radar of the present invention.

Specifically, as shown in FIGS. 1 and 4, the millimeter wave radar emits fixed frequency electromagnetic waves through its own antenna, and then synchronously receives electromagnetic wave reflections. By changing the frequency and angle of the reflected signal, it collects the information on the movement amplitude and the azimuth of the moving object. The movement amplitude of the millimeter wave radar is divided into three levels: signal intensity of the moving object, signal intensity of breathing movement, and motion intensity of human heartbeat. The azimuth information is divided into three dimensions of distance information: X (horizontal and ground distance information of the radar), Y (distance information of the moving object from the radar), and Z (vertical height information of the object to the ground). By overlaying the information from different dimensions mentioned above, different vital signs of people can be analyzed and determined: based on the intensity of major movements and changes in the azimuth information of point clouds, the movement state of people (active & stationary), their flipping over, getting up, and even struggling situations can be analyzed; based on the intensity of breathing movements, the breathing depth and frequency can be analyzed; the heartbeat frequency and other factors can be analyzed based on the heartbeat motion intensity. Based on the different vital sign information of people analyzed by the millimeter wave radar above, a series of determinations on sleep are made: when to get in/leave bed, when to start entering sleep, whether to be awake, light to sleep, or deep to sleep during sleep, whether to get up midway through sleep, integrating a whole segment of sleep information to output a sleep report (as shown in FIG. 2), and evaluating the sleep quality (as shown in FIG. 3); in order to achieve basic care for daily sleep health of people, and to link lighting and sleep aid music based on real-time changes in sleep state, and assisting in improving people's sleep quality.

Finally, it should be noted that the above is only a preferred embodiment of the present invention and is not intended to limit the present invention. Although the present invention is illustrated with reference to the above embodiments, those skilled in the art can still modify the technical solutions described in the above embodiments, or equivalently replace some technical features therein, and any modification, equivalent replacement, improvement, etc. made within the spirit and principle of the present invention shall be included in the protection scope of the present invention.

The invention claimed is:

1. A lamp control method based on biometric data, characterized by comprising the following steps:
   a getting-up monitoring step: obtaining a point cloud height of center of gravity of each point in point cloud azimuth data detected by a millimeter wave radar;
   a half getting-up evaluation step: determining whether the number of points with a preset height threshold of center of gravity triggered by point cloud height of center of gravity within a first set time exceeds a preset half getting-up threshold, if yes, determining it as a half getting-up action;
   a full getting-up evaluation step: determining whether the number of points with a preset height threshold of center of gravity triggered by point cloud height of center of gravity within a second set time exceeds a preset full getting-up threshold, if yes, determining it as a full getting-up action; and
   a first lamp control step: if a subject has a half getting-up action, controlling the lamp to work in a first state, and if a subject has a full getting-up action, controlling the lamp to work in the second state.

2. The lamp control method based on biometric data according to claim 1, characterized in that, the full getting-up evaluation step comprises: determining whether it is a half getting-up action in the half getting-up evaluation step, if yes, determining whether the number of points with a preset height threshold of center of gravity triggered by point cloud height of center of gravity within a second set time exceeds a preset full getting-up threshold, if yes, determining it as a full getting-up action.

3. The lamp control method based on biometric data according to claim 1, characterized by further comprising before the getting-up monitoring step:

a detection step: obtaining biometric data generated by reflected waves of a millimeter wave radar, the biometric data including point cloud azimuth data and a subject's energy intensity;

an in-bed evaluation step: analyzing an average breathing frequency based on the subject's energy intensity, and determining whether the average breathing frequency triggers a preset in-bed breathing threshold, if yes, determining whether the subject is within a preset detection boundary, if yes, determining it as the in-bed state;

an off-bed evaluation step: determining whether the subject has left the preset detection boundary, if yes, determining whether the radar has detected the subject's energy intensity, if not, starting to accumulate the time the subject has left the detection boundary; if the accumulated time triggers the preset off-bed duration threshold, determining it as the off-bed state; and a getting-up monitoring step: determining whether it is in an in-bed state in the in-bed evaluation step, if yes, monitoring the point cloud height of center of gravity of each point in point cloud azimuth data detected by a millimeter wave radar in real time.

4. The lamp control method based on biometric data according to claim 3, characterized by further comprising the following step:

a gesture wake-up step: detecting point cloud azimuth data and velocity values based on electromagnetic wave signal reflection in real time, determining whether the point cloud orientation data triggers a preset gesture threshold, if yes, determining whether the velocity value triggers the preset gesture velocity threshold, if yes, controlling the lamp to turn on.

5. The lamp control method based on biometric data according to claim 3, characterized by further comprising after the detection step:

a someone presence evaluation step: determining whether to meet a preset someone presence determination condition through point cloud azimuth data detected by the millimeter wave radar and motion intensity based on energy intensity, if yes, determining it as a someone presence state;

an approaching evaluation step: determining whether to meet a preset approaching determination condition through motion intensity and point cloud azimuth data detected by the millimeter wave radar, if yes, determining it as an approaching action;

a second lamp control step: the lamp including a clock lamp and a main lamp; determining whether it is in the someone presence state in the someone presence evaluation step, if yes, controlling the clock lamp to turn on; determining whether it is an approaching action in the approaching evaluation step, and if yes, controlling the main lamp to turn on; determining whether it is in the off-bed state in the off-bed evaluation step, if yes, turning off the lamp; determining whether it is in the in-bed state in the in-bed evaluation step, if yes, turning off the lamp;

further comprising between the someone presence evaluation step and the half getting-up evaluation step; and a motion sign analysis step: dividing the detected real-time energy intensity into N parts and determining whether the energy intensity is only related to breathing and/or heartbeat motion intensity, if yes, assigning a value of 1 to the motion sign parameter, if no, associating the motion sign parameter with the motion intensity, with a value range of 2 to N;

further comprising after the motion sign analysis step:

a walking-around evaluation step: determining whether the motion sign parameter in the motion sign analysis step is 1, if yes, associating the motion sign parameter with the motion intensity, and determining whether the motion sign parameter triggers a preset walking-around threshold, if yes, determining it as a walking-around action, and turning on the main lamp.

6. The lamp control method based on biometric data according to claim 5, characterized by further comprising after the someone presence evaluation step:

a voice activation step: determining whether it is in the someone presence state in the someone presence evaluation step, if yes, activating a voice device;

further comprising after the voice activation step and the motion sign analysis step:

a struggling evaluation step: determining whether the motion sign parameter in the motion sign analysis step is 1, if yes, associating the motion sign parameter with the motion intensity, and determining whether the motion sign parameter triggers a preset struggling threshold, if yes, determining it as a struggling action;

an inquiry wake-up step: determining whether it is determined as a struggling action in the struggling evaluation step, if yes, the voice device will emit a preset inquiry voice;

a getting-up prompt step: determining whether it is in the full getting-up state in the full getting-up evaluation step, if yes, the voice device will emit a safety voice;

an early warning step: determining whether there is a response to the inquiry voice, if no, repeating the inquiry wake-up step; and an alarm step: determining whether the inquiry wake-up step is repeated no less than 2 times, if yes, reporting the alarm information to a server.

7. A sleep monitoring method, characterized by, controlling a lamp using the lamp control method based on biometric data according to claim 1, the sleep monitoring method further comprises the following steps:

a preset step: presetting at least two deep sleep duration value ranges, at least two light sleep duration value ranges, at least two getting-up frequency value ranges, at least two average breathing frequency value ranges, and at least two flipping-over frequency value ranges, and assigning corresponding scores to each value range;

a value acquisition step: calculating the deep sleep duration value, light sleep duration value, getting-up frequency value, average breathing frequency value, and flipping-over frequency value based on the biometric data collected by the millimeter wave radar;

a scoring step: mapping the deep sleep duration value to the deep sleep duration value range, and obtaining the deep sleep rating value; mapping the light sleep duration value to the light sleep duration value range, and obtaining the light sleep score value; mapping the getting-up frequency value to the getting-up frequency value range, and obtaining the getting-up score value;

mapping the average breathing frequency value to the average breathing frequency value range, and obtaining the breathing score value; mapping the flipping-over frequency value to the flipping-over frequency value range, and obtaining the flipping-over score value; and an overall evaluation step: adding the deep sleep score value, light sleep score value, getting-up score value, breathing score value, and flipping-over score value to obtain the total sleep score.

8. The sleep monitoring method according to claim 7, characterized by further comprising between the detection step and the value acquisition step:

a sleep state evaluation step: determining whether it is in the in-bed state in the in-bed evaluation step, if yes, performing a sleep state determination every a predetermined time period, the sleep state including a waking state, a light sleep state, and a deep sleep state, and obtaining the deep sleep duration value and the light sleep duration value;

a flipping-over evaluation step: determining whether to be determined as the in-bed state in the in-bed evaluation step, if yes, monitoring point cloud azimuth data detected by the millimeter wave radar and motion intensity based on energy intensity in real time, and determining whether the motion intensity is enough to trigger the preset flipping-over threshold, if yes, determining whether the point cloud azimuth data is enough to trigger the preset point cloud change threshold, if yes, determining it as a flipping-over action and recording the flipping-over frequency;

a physiological parameter analysis step: screening out an energy range that matches the real breathing change based on the analysis of real-time energy intensity detected by the millimeter wave radar, and converting the frequency to obtain the breathing rate; and a value acquisition step: obtaining the deep sleep duration value and the light sleep duration value based on the sleep state evaluation step, obtaining the getting-up frequency value based on the off-bed evaluation step, obtaining the average breathing frequency value based on the physiological parameter analysis step, and obtaining the flipping-over frequency value based on the flipping-over evaluation step.

9. A lamp control device based on biometric data, characterized by comprising:

a detection module: used for obtaining point cloud azimuth data generated by reflected waves of a millimeter wave radar and a subject's biometric data;

an in-bed evaluation module: used for analyzing an average breathing frequency based on the subject's energy intensity, and determining whether the average breathing frequency triggers a preset in-bed breathing threshold, if yes, determining whether the subject is within a preset detection boundary, if yes, determining it as the in-bed state;

an off-bed evaluation module: used for determining whether the subject has left the preset detection boundary, if yes, determining whether the radar has detected the subject's energy intensity, if not, starting to accumulate the time the subject has left the detection boundary; if the accumulated time triggers the preset off-bed duration threshold, determining it as the off-bed state;

a getting-up monitoring module: used for determining whether it is in an in-bed state in the in-bed evaluation step, if yes, monitoring the point cloud height of center of gravity of each point in point cloud azimuth data detected by a millimeter wave radar in real time;

a half getting-up evaluation module: used for determining whether the number of points with a preset height threshold of center of gravity triggered by point cloud height of center of gravity within a first set time exceeds a preset half getting-up threshold, if yes, determining it as a half getting-up action;

a full getting-up evaluation module: determining whether the number of points with a preset height threshold of center of gravity triggered by point cloud height of center of gravity within a second set time exceeds a preset full getting-up threshold, if yes, determining it as a full getting-up action; and a first lamp control module: used for, if a subject has a half getting-up action, controlling the lamp to work in a first state; if a subject has a full getting-up action, controlling the lamp to work in the second state.

\* \* \* \* \*